United States Patent [19]

Longini

[11] 4,380,167
[45] Apr. 19, 1983

[54] APPARATUS AND METHOD FOR DETECTING A FRACTION OF A GAS

[75] Inventor: Richard L. Longini, Pittsburgh, Pa.

[73] Assignee: Energy Controls, Inc., Denver, Colo.

[21] Appl. No.: 245,108

[22] Filed: Mar. 18, 1981

[51] Int. Cl.³ .......................................... G01N 29/02
[52] U.S. Cl. .................................................. 73/24
[58] Field of Search ................................ 73/24, 23, 29

[56] References Cited

U.S. PATENT DOCUMENTS 2,283,750  5/1942  Mikelson .................................. 73/24
3,011,718  12/1961  Joerren et al. ........................... 73/24
3,981,176  9/1976  Jacobs ..................................... 73/24

OTHER PUBLICATIONS

Publication "Gas Chromatographic Detectors", D. J. David (1974), Wiley, pp. 144-164.
Publication "Instrumental Methods of Analysis", Third Edition 1958, D. Van Nostrand Co., p. 341.
Publication "Continuous Analysis of Chemical Process Systems", Sidney Siggia, 1959, Wiley & Son.

*Primary Examiner*—Stephen A. Kreitman
*Attorney, Agent, or Firm*—Buell, Blenko, Ziesenheim & Beck

[57] ABSTRACT

An apparatus is provided for detecting the quantity of a specific gas hereinafter simply called "gas" in a carrier gas when water vapor is present. The gas and the carrier gas are passed through a whistle chamber which produces a resonating frequency. The resonant frequency changes as a function of the fraction of the gas, temperature and water vapor. An output signal is produced which is a function of the resonant frequency. A correction device senses water vapor and temperature and produces an output signal which is a function of the water vapor and the temperature. A receiving means receives the output signals and produces a resultant signal which is a function of only the fraction of the gas.

5 Claims, 6 Drawing Figures

APPARATUS AND METHOD FOR DETECTING A FRACTION OF A GAS

The invention relates to an apparatus and method for detecting a fraction of a specific gas hereinafter called "gas" in a carrier gas under any temperature when water vapor is present.

PROBLEM PRESENTED TO THE INVENTOR

Carbon dioxide is the principal product of the oxidation process in human respiration. Other end products are minor. The metabolism of carbohydrates produces $CO_2$ but does not use any oxygen to make the water that is released. One can equate, within a good approximation the amount of oxygen used in respiration to 83% of the $CO_2$ in a habitation if no material such as methane ($CH_4$) is being consumed in the space. Depending on food consumed, etc., the percent can vary from this (83%). In any case some practitioners claim that the measure of $CO_2$ is more important than the amount of oxygen present. Therefore in theaters, most classrooms, and other public places, the measure of $CO_2$ will be an excellent indicator of the degree to which the oxygen in the air has been exhausted. The ventilation systems of these places can be regulated by monitoring the quantity of $CO_2$ detected in the air. Thus, the precision needed for the $CO_2$ monitor is only about one-tenth of that needed for the $O_2$ monitor.

Devices which measure the quantity of a gas in a carrier gas have been considered. These devices employ the principle that the velocity of ultrasonic waves in a gas is dependent on the specific heats and moleuclar weight. The variation in the velocity of sound waves in a gas can then be used to determine the varying compositions of the gas. Such a system is described in "Continuous Analysis of Chemical Process Systems" by Sidney Siggia (chapter 18, p. 277), John Wiley & Son 1959. Other devices using the principle are described in "Instrumental Methods of Analysis" (Third Edition, 1958), D. Van Nostrand Company (p. 341); and "Gas Chromatographic Detectors" by D. J. David, Wiley, 1974 (pp. 144-164). Temperature and water vapor affect the velocity and the resonant frequency of the gas.

These devices employ a fixed frequency. Phase shift is used as the detection means. The relative phase of the receiving signal from that of the transmitting signal is determined and an output is produced which is related to the phase difference. These devices remove all other trace gases and are worked at a fixed temperature. These devices are not suitable for the type of control which is needed to control a ventilation system in an environment in which water vapor is present and together with temperature, changes frequently. The devices do not take into account the effects of temperature and water vapor on the velocity of the gas.

THE INVENTOR'S SOLUTION TO THE PROBLEM

The inventor uses a chamber through which a foreign gas to be measured passes. A resonant frequency of the gas is developed in the chamber. The resonant frequency changes and is a function of the fraction of the gas being measured, water vapor and temperature. The resonant frequency is determined and a corresponding output signal is produced.

Devices sense water vapor and temperature of the gas and a corresponding output signal is produced.

The output signals are received and processed and an output signal is produced which is a function of only the quantity of the gas such as carbon dioxide. This signal can be used to control a ventilation system in a public place. The amount of oxygen input to an area can be increased or decreased depending upon the amount of carbon dioxide present. The system also can be used in a multiplexed mode. In this mode a plurality of chamber, water vapor and temperature sensing devices and receiving means are used and can collectively produce an output signal which can regulate a ventilation system.

DESCRIPTION OF THE INVENTOR'S APPARATUS AND METHOD FOR DETECTING THE QUANTITY OF A GAS

Figure 1:
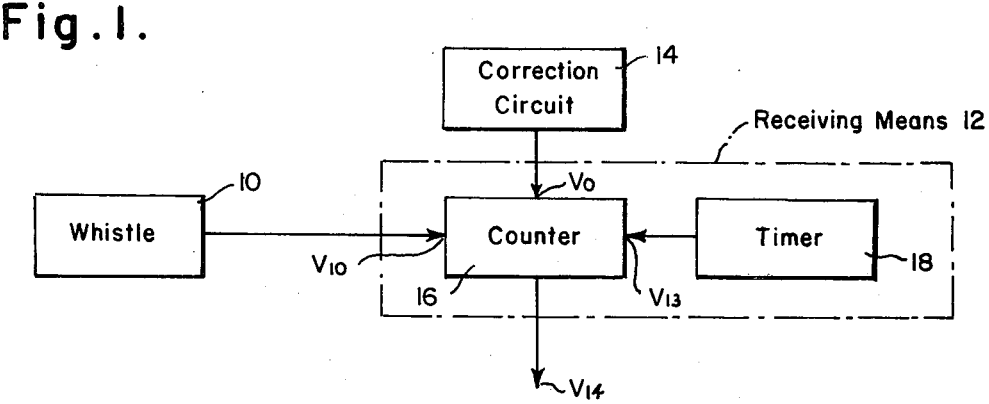
FIG. 1 is a block diagram of the apparatus.

FIG. 1 shows a block diagram of the apparatus in which a whistle means 10 has its output signal $V_{10}$ coupled to a receiving means circuit 12. A correction means circuit 14 also has its output signal $V_0$ connected to the receiving means circuit 12. The receiving means circuit 12 includes a counter circuit 16 and a timer circuit 18. The receiving means circuit 12 produces an output signal $V_{14}$ which is a function of a fraction of gas which is passed with a carrier gas through the whistle means 10. Assuming that the carrier gas is air and the quantity of gas desired to be measured in the carrier gas is carbon dioxide, the $V_{14}$ signal can be used to activate the controls of a ventilation system in a building.

Whistle Means (10)

Figure 2:
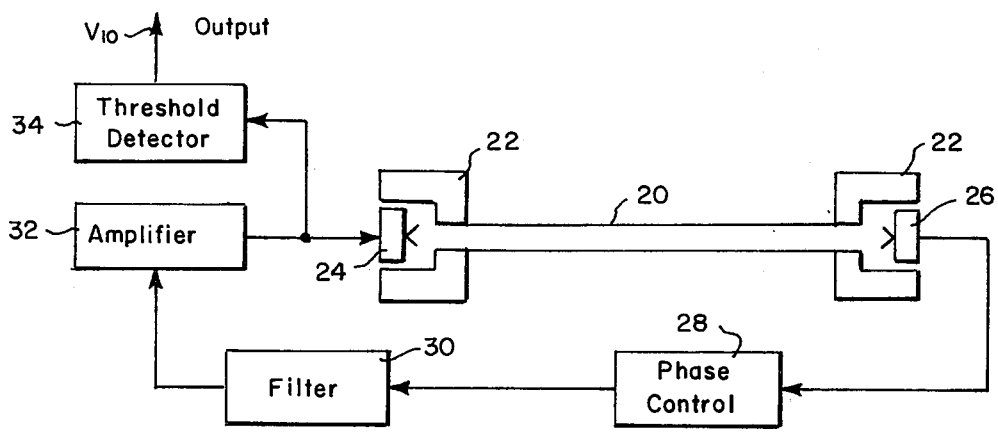
FIG. 2 is a block diagram of the whistle.

FIG. 2 shows the whistle means 10 which comprises a chamber tube 20 which acts as a resonator. It is a number of wave lengths long and can be as long as ten wave lengths. The wave lengths would be those for the natural resonating frequency of the particular gas whose fraction is to be measured. In this instance because $CO_2$ is the gas to be measured an appropriate length for the tube 20 would be 8.5 to 10 cm. In order to make the gas such as carbon dioxide resonant in the tube 20 it must be driven. A resonant frequency is one where vibrations of the total gas in the tube 20 continue and, along with the energy supplied from the auxilliary circuits, will be self exciting.

Baffle 22 prevents sound from going around tube 20. A drive crystal 24 produces sonic movement of air. In this particular system the air is moved at a frequency of approximately 40 kHz. Although it is to be understood that other frequencies can be used a representative range of frequencies that can be used are 38 to 40 kHz. The tube used is stainless steel of stable dimensions. The inside diameter is 0.17 cm. The ends of the tube are tapered so that the wall thicknesses are reduced substantially at the end. This prevents the metal from coupling with the vibrating air between it and the crystals. The tube 20 begins about one quarter of a wave length from acoustic drive crystal 24 and ends one quarter of a wave length from acoustic receiving crystal 26. Sound travels from the drive crystal 24 down the gas and carrier gas to the receiving crystal 26. The output signal from the receiving crystal 26 goes to a phase control 28; band pass filter 30; amplifier 32; and back to the driving crystal 24. The purpose of the phase control 28 is to insure that the signal from the receiving crystal 26 going to the driving crystal 24 is in the proper phase with the driving crystal 24 so that it builds resonance instead of counteracting it. It avoids causing the surface of crystal 24 to move to the left when the resonance would move it to the right. The frequency at which it will resonate is one where the phase around the loop must be some multiple of 360°. The filter 30 is to permit only frequencies in a certain range to be amplified so that a resonance can be set at the frequency desired. The output of amplifier 32 also goes to a threshold detector 34 which determines whether the signals are of sufficient amplitude to be considered to be resonant and if so then every amplitude that crosses the threshold causes a pulse which becomes the output signal $V_{10}$ of the whistle means 10. The output $V_{10}$ of the whistle means 10 goes to the counter 16 which is part of the receiving circuit means 12.

Assuming that the quantity of gas to be determined is $CO_2$ then the monitoring is based on the decreased sound velocity found when the fraction of $CO_2$ in air is increased. For a resonant sound in tube 20 the frequency of resonance will decrease with small increases of $CO_2$ concentration. The velocity of sound is dependent on the density of a gas mixture as well as on temperature and certain adiabatic parameters of the components. Approximately the square of the velocity is inversely proportional to the density divided by the pressure (and is thus independent of pressure for an ideal gas). The ratio of the adiabatic constants (specific heat ratios) for air and $CO_2$ is 1.05 in the direction to enhance the density effect. The density of pure $CO_2$ is 1.51 times that of dry air, thus it greatly influences sound velocity. For a variation of $CO_2$ from 1.15% to 1.20% we therefore expect a velocity change of about 0.0115%. Thus, a resonant frequency of 40,000 Hz would change to 39,995.4 Hz, which is an easily detectable difference.

Water vapor and temperature are other factors which influence the resonant frequency. Water vapor has a mass of only 62% of an equal number of molecules of dry air. The adiabatic factor for $H_2O$ reduces the influence of water vapor by about 5%. The dependance of both temperature and water vapor is known and can be corrected analytically when the absolute humidity and temperature are known. An approximate equation for small deviations from pure air for the frequency of the air filled resonator as a function of $CO_2$ content, absolute humidity, and temperature is:

$$\text{Resonant frequency} = F_o(1 - .231h + .165k)\sqrt{vT}$$

where $F_o$ is the constant of proportionality depending on resonator dimensions, T is the temperature in degrees Kelvin of the resonator, h is the molecular fraction of $CO_2$ in the resonator, k is the molecular fraction of $H_2O$ in the resonator.

The velocity of sound in tube 20 is what determines the frequency. The higher the velocity the higher the frequency. The velocity is reduced by the presence of carbon dioxide assuming that is the gas that is being measured. The velocity will be increased by the presence of water vapor which is lighter than air and it will be substantially increased by the presence of hydrogen. Also, the velocity (and frequency) is dependant upon temperature.

Receiving Circuit Means (12)

The receiving circuit means 12 comprises a counter circuit 16 and a timer 18. The counter 16 counts the number of pulses there are in a given length of time and thereby indicates the resonant frequency of the system in the whistle means 12. The purpose of the counter 16 is to provide a final output $V_{14}$ for the control or display of the concentration of the gas (or $CO_2$, $H_2$ or whatever foreign gas is in the carrier gas). There are a number of various counter circuits commercially available which are adequate for these purposes. Decade counter number 74192 can be used. The counter circuit 16 counts pulses for a certain length of time. It counts the number of cycles the whistle means 10 has undergone in a particular length of time determined by the timer 18.

Correction Means (14)

Figure 3:
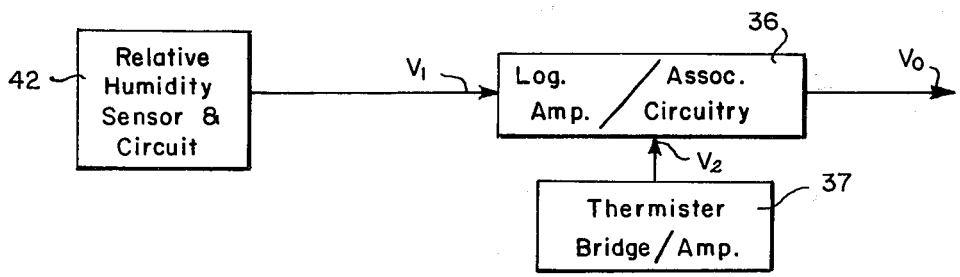
FIG. 3 is a block diagram of the correction circuit.

FIG. 3 shows the block diagram for the correction circuit means 14 which produces an output signal $V_0$.

Figure 4:
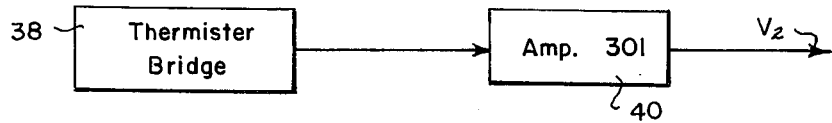
FIG. 4 is a block diagram of the thermister bridge circuit.
Figure 5:
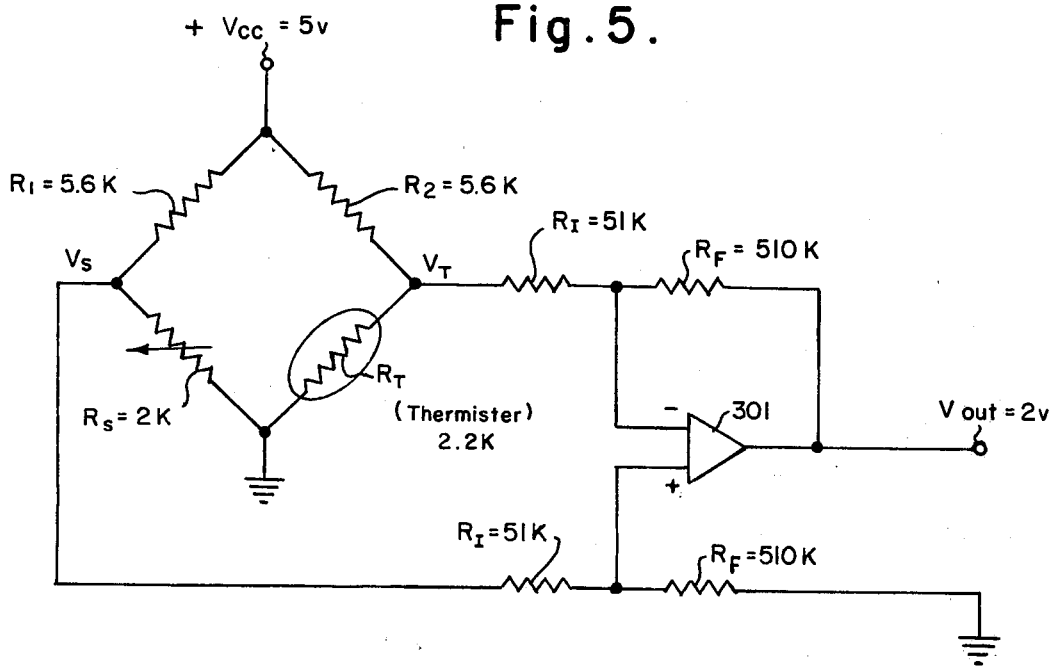
FIG. 5 is a schematic of the thermister circuit.

It is necessary to make corrections for the absolute amount of water and temperature present. Temperature is measured by a thermister which is in a thermister bridge circuit 38 which is coupled to an amplifier 40 which produces an output signal $V_2$. There are many standard thermisters on sale for measuring temperature with adequate precision for this purpose. The schematic for this circuit 38 and the amplifier 40 in the block diagram in FIG. 4 is shown in detail in FIG. 5. The water vapor or absolute humidity is a function of relative humidity and temperature. The determination of the resonant frequency as influenced by temperature and water vapor is shown in the above equation.

Figure 6:
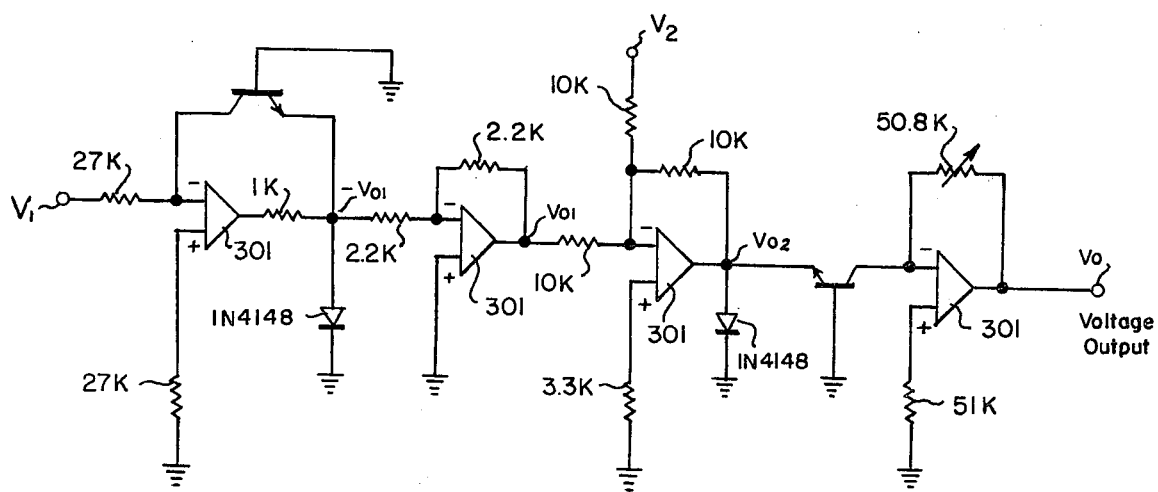
FIG. 6 is a schematic of the correction circuit.

A humidity device 42 (FIG. 3) is used to sense the relative humidity. Such a device and circuit is shown by James Williams of National Semiconductor and is published in the *Electronic Design News* "An Elegant G-1c Circuit Gauges Relative Humidity", June 5, 1980 (p. 149). The sensing device is a PCRC-11 sensor by Phys-Chem Corp. This circuit has an output $V_1$ which is coupled to a log amplifier and other associated circuitry 36. The log amplifier and other associated circuitry 36 (shown in detail in the schematic in FIG. 6) produces an output signal $V_0$. It is to be understood that the thermister and the humidity sensor can be either within the chamber tube 20 or within the same environment. It also must be understood that the circuits shown in FIGS. 5 and 6 were not adjusted for the particular humidity sensor used and some adjustment may have to be made to the circuits shown.

OPERATION OF THE RECEIVING CIRCUIT MEANS (12)

The timer 18 activates an 80 kHz generator which is considered part of the timer means 18. Pulses are provided for the period set by the timer. This timing may be as little as 10 microseconds or as high as several milliseconds. The timing controls the number of pulses that are put out by the 80 kHz generator. The pulses are used to count down the input to the counter 16 in a count down mode. The whistle 10 input signal $V_{10}$, however, is in a count up mode. The result is that depending upon the temperature and absolute humidity as reflected by $V_o$ from the correction circuit 14 to the counter 16, a correction in the number of counts is observed. Therefore, while the whistle 10 may oscillate at 40,236 Hz, the correction for temperature and humidity count down may be 236 which would provide a net value of 40,000 Hz which would be the $V_{14}$ output from the counter 16. The count can be calibrated for pure air. The difference in count will indicate how much $CO_2$ is present and the corresponding output signal $V_{14}$ can be used to control the flow of fresh air into a room by controlling ventilation, damper motors or indicating the amount of $CO_2$ (or whatever gas is involved) by a meter.

If the particular gas involved is hydrogen, then the velocity of the gas is higher than the velocity of pure air and the count from the counter will exceed 40,000 by an amount proportional to this amount of hydrogen present.

The counters can be reversed in direction, i.e. the whistle will cause a count down from same pre-set initial value. The correction circuit will also operate in the reverse direction. If the pre-set value is so chosen that for pure air the count down would go to zero in the alotted time, then the residue would be proportional to the fraction of $CO_2$. Similarly, if $H_2$ were the gas under scrutiny, a count up from same negative pre-set number would go to zero for pure air, and any excess count from the whistle would be proportional to the fraction of $H_2$ present. In either case a suitable choice of timing could make it so the residual counts would be in units of 1/100% of the gas fraction, for example.

The apparatus can be grouped with other identical equipment and coupled to a multiplex device (not shown) which produces an output signal that can be used to control ventilation or other equipment.

I claim:

1. An apparatus for detecting a fraction of a gas in a carrier gas when water vapor is present comprising:

(a) whistle means which has a resonant frequency and through which the gas and the carrier gas are passed, the resonant frequency changes as a function of the fraction of the gas, a temperature of the gas, and the water vapor and produces a whistle means output signal which is a function of the resonant frequency;
   (b) correction means which senses the water vapor and the temperature and produces a correction means output signal which is a function of the water vapor and the temperature; and
   (c) receiving means receiving the whistle means output signal and the correction means output signal and producing an output signal which is only a function of the fraction of the gas, the receiving means having:
      (i) a timer means which produces a timer means output signal for a preset time; and
      (ii) a counter means receiving the whistle means output signal, correction means output signal and the timer means output signal and producing an output signal which is only a function of the fraction of the gas.

2. An apparatus as recited in claim 1 wherein the whistle means includes:

(a) a chamber through which the gas and the carrier gas are passed, the chamber having a transducer at each end of the chamber; and
   (b) an amplifier coupled to one of the transducers for amplifying a signal from the other transducer.

3. An apparatus as recited in claim 2 including a phase shift means for controlling the phase of the signal input to the amplifier with the frequency of the gas at the transducer coupled to an output of the amplifier.

4. An apparatus as recited in claim 2 including a threshold detector coupled to the output of the amplifier.

5. An apparatus as recited in claim 3 including a band pass filter coupled to the amplifier.

* * * * *